United States Patent
Arduengo, III

(10) Patent No.: US 7,868,182 B2
(45) Date of Patent: Jan. 11, 2011

(54) SOLVENTLESS ONE-STEP PROCESS FOR THE PRODUCTION OF IMIDAZOLE-2-THIONES

(76) Inventor: Anthony J. Arduengo, III, P.O. Box 760, Coaling, AL (US) 35449

( * ) Notice: Subject to any disclaimer, the term of this patent is extended or adjusted under 35 U.S.C. 154(b) by 833 days.

(21) Appl. No.: 11/622,883

(22) Filed: Jan. 12, 2007

(65) Prior Publication Data

US 2008/0171883 A1    Jul. 17, 2008

(51) Int. Cl.
*C07D 233/30* (2006.01)
(52) U.S. Cl. .................................. 548/325.1
(58) Field of Classification Search ............... 548/325.1
See application file for complete search history.

(56) References Cited

U.S. PATENT DOCUMENTS

| | | | |
|---|---|---|---|
| 5,030,644 A * | 7/1991 | Baldwin et al. | ............. 514/393 |
| 5,077,414 A | 12/1991 | Arduengo, III | |
| 5,104,993 A * | 4/1992 | Arduengo, III | ........... 548/316.4 |
| 5,162,482 A | 11/1992 | Arduengo, III | |
| 5,198,457 A | 3/1993 | Yarrington | |
| 5,554,211 A | 9/1996 | Bokisa | |
| 5,962,586 A | 10/1999 | Harper | |
| 6,395,948 B1 * | 5/2002 | Hope et al. | ................. 585/510 |
| 7,115,748 B2 | 10/2006 | Grast | |
| 2003/0094380 A1 * | 5/2003 | Moulton | ..................... 205/431 |

OTHER PUBLICATIONS

Nguyen et al.,"Ionic Liquids as Catalytic "Green" Reactants and Solvents for Nucleophilic Conversion of Fatty Alcohols to Alkyl Halides", Green Chemistry, 5, 303-305, 2003.*
Freemantle, "Designer Solvents: Ionic Liquids May Boost Clean Technology Development", Chemical and Engineering News, 32-37, Mar. 30, 1998.*
Holbrey, "Industrial Applications of Ionic Liquids", Chemistry Today, 35-37, Jun. 2004.*
Tao et al., "Unexpected Microwave Reaction of 1,3-Disubstituted Imidazolium Salts: A Novel Synthesis of 1,3-disubstituted Imidazole-2-thiones", Synthetic Communications, 37(3),399-408, 2007.*
Karkhanis et al., STN, file CASREACT, Abstract No. 103:53997, 1985, "Thiono Compounds. 5. Preparation and Oxidation of Some Thiono Derivatives of Imidazoles".*
Lei et al., STN, file CASREACT, Abstract No. 145;83328, 2005, CN 1680337, "Microwave Irradation Solvent-Free Method for Synthesis of 1,3-Disubstituted 4-Imidazoline-2-thiones".*
Parnham et al., "1-Alkyl-3-Methyl Imidazolium Bromide Ionic Liquids in the Ionothermal Synthesis of Aluminum Phosphate Molecular Sieves", Chem. Mater., 18(20), 4882-4887, 2006.*
Nelson, "Are Ionic Liquids Green Solvents?", 818 ACS Symposium Series, 30-41, (American Chemical Society 2002).*
Freemantle, "Eyes On Ionic Liquids", Chemical and Engineering News, 78(20), 37-50, May 15, 2000.*
Ren et al., Chemical Abstracts, Abstract No. 2002:617123, 2002.*
Chowdhury et al., "Reactivity of Ionic Liquids", Tetrahedron , 63, 2263-2389, available online Dec. 8, 2006.*
Trzhtsinskaya, Bella V. et al., "Imidazole-2-Thiones: Synthesis, Structure, Properties", Journal of Sulfur Chemistry, 10(4), 389-421, Jun. 1991.*
Benac, B.; Burgess, E. M.; Arduengo, III, A. J. "The Synthesis of 1,3-Dimethylimidazole-2-thione", Organic Syntheses, vol. 64, pp. 92-95, 1986.
Biegel, L. B. et al.. "Subchronic Toxicity Study in Rats with 1-Methyl-3-propylimidazole-2-thione (PTI): Effects on the Thyroi" Fundamental and Applied Tox., 27, 185-94, 1995.
Arduengo, III, A. J. et al. "Electron Distribution in a Stable Carbene" J. Am. Chem. Soc. 116, 6812-22, 1994.

* cited by examiner

*Primary Examiner*—Fiona T Powers

(57) ABSTRACT

A novel solventless process is described for the preparation of imidazole-2-thiones. The new solventless process tolerates a variety of bases as co-reactants which introduces feedstock flexibility into the process while the solventless feature renders the process more environmentally friendly by eliminating volatile organic solvents from the process, reducing energy consumption (associated with solvent recovery and/or recycling), and allows shorter reaction time and workup. Furthermore, the elimination of solvents enhances workplace safety by obviating the need for flammable and/or toxic solvents.

20 Claims, No Drawings

SOLVENTLESS ONE-STEP PROCESS FOR THE PRODUCTION OF IMIDAZOLE-2-THIONES

FIELD OF THE INVENTION

The present invention provides a new manufacturing process for the production of imidazole-2-thiones. This new process does not require the use of solvent and can be performed as a single-step in a single reaction vessel.

BACKGROUND OF THE INVENTION

Imidazole-2-thiones are chemical compounds with relatively low toxicity [L. B. Bieqel, et al., *Fundamental and Applied Toxicology*, 27, 187-94, 1995] frequently used as substitutes for thioureas and have wide-spread applications such as chemical intermediates, catalysts for crosslinking adhesives [U.S. Pat. No. 5,296,586 Harper, 1999] and coatings [U.S. Pat. No. 5,162,482, Arduengo, 1992], activators for electroless plating [U.S. Pat. No. 5,554,211, Bokisa et al., 1996] and pharmaceuticals [U.S. Pat. No. 5,198,457, Yarrington, 1993].

These imidazol-2-thiones have been prepared by reacting vicinal diamines with compounds having a thiocarbonyl moiety and subsequently oxidizing the resulting reaction product [U.S. Pat. No. 7,115,748, Grast et al., 2006]; by reacting an imidazolium salt, sulfur and potassium carbonate in methanol solvent [B. Benac, et al., *Organic Syntheses*, vol. 64, pp. 92-95, 1986]; or by contacting an imidazolium salt with sulfur and sodium methoxide in an alcohol solvent [U.S. Pat. No. 5,104,993, Arduengo, 1992]. The afore mentioned conventional syntheses have various drawbacks including the use of solvents and, in some cases, multiple steps and/or protection/deprotection schemes. The alcohol solvent-based procedures suffer from the additional disadvantage that only a limited number of bases perform well in the reactions and the product imidazole-2-thione must be carefully purified to remove a malodorous reaction by-product.

The current invention provides a convenient solvent-free one-step route to a broad class of imidazole-2-thiones.

SUMMARY OF THE INVENTION

The present invention is a procedure that enables the reaction of imidazolium salts bearing a hydrogen at the C-2 position with range of bases and elemental sulfur in the absence of a solvent to produce imidazole-2-thiones. This invention enhances workplace safety by obviating the need for flammable and/or toxic solvents and the product imidazole-2-thiones are free from malodorous by-products that are produced when alcohols are present during the reaction as in conventional procedures.

DETAILED DESCRIPTION OF THE INVENTION

This invention provides a general method to convert a di-, tri-, or tetra-substituted imidazolium salt to a di-, tri-, or tetra-substituted imidazole-2-thione (respectively) through the use of a solventless process involving reaction with sulfur in the presence of a base. The starting imidazolium salts for the process are of the general formula:

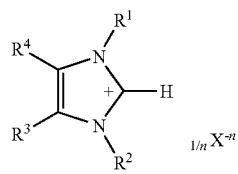

wherein:

$R^1$ and $R^2$ are independently hydrocarbyl or substituted hydrocarbyl;

$R^3$ and $R^4$ are independently hydrogen, hydrocarbyl, substituted hydrocarbyl, ether, or thioether;

$X^{-n}$ is an anion that is the counterion to the imidazolium cation. The anion $X^{-n}$ may be a simple inorganic monoanion (n=1) such as halide, nitrate, triflate, hexafluorophosphate, or tetrafluoroborate. Anions bearing additional acidic protons such as bisulfate, or dihydrogenphosphate can also be employed in the reaction if the base stoichiometry is increased to compensate for the additional acidic protons introduced from the anion. Organic anions such as acetate, trifluoroacetate, or benzoate may also be employed as counterions for the imidazolium cation of the starting material. Polyanions such as sulfate (a dianion, n=2) or phosphate (a trianion, n=3) may also be employed as counterions to the starting imidazolium cation.

The term "hydrocarbyl" is used herein to mean any substituent group that is composed of only carbon and hydrogen atoms in any connectivity (linear or branched), cyclicity (cyclic or acyclic), chirality (and achiral), saturated or unsaturated. The term "hydrocarbyl" thus may include alkyl, aryl, olefinic, or acetylenic moieties, alone or in combination. The term "substituted hydrocarbyl" is used herein to mean a hydrocarbyl moiety that bears any substituent group which does intra- or inter-molecularly react with another portion of the imidazolium salt precursor, the imidazole-2-thione product, or another component of the reaction process and render the substance unstable or unusable in the reaction process. For example suitable substituents include, but are not limited to, cyano, ether, thioether, ester, halo, primary amino, substituted amino, halo, hydroxy, vinyl, and substituted imidazoles. Certain acidic groups such as carboxylic acids, sulfonic acids, and phosphonic acids may also be tolerated in the reaction even though they react with the base component of the reaction process because the base stoichiometry can be adjusted to compensate for the additional acid residues and the deprotonation of these acid groups is reversible at the end of the reaction process.

The starting material imidazolium salts for this new process are readily available through a variety of established syntheses such as alkylation of imidazoles with alkyl halides [Benac, 1986; U.S. Pat. No. 5,104,993 Arduengo 1992], and condensation of formaldehyde with α-diketones and substituted amines in the presence of an acid. [U.S. Pat. No. 5,077,414 Arduengo 1991].

The product of this invention is a substituted imidazole-2-thione of the general formula:

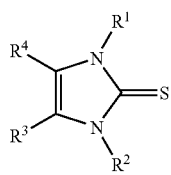

wherein:

$R^1$ and $R^2$ are independently hydrocarbyl or substituted hydrocarbyl;

$R^3$ and $R^4$ are independently hydrogen, hydrocarbyl, substituted hydrocarbyl, ether, or thioether.

The terms "hydrocarbyl" and "substituted hydrocarbyl" are as defined above.

Preferred substituents on the nitrogens ($R^1$ and/or $R^2$) include alkyl groups from 1 to 12 carbon atoms or aryl groups of at least 6 atoms. More preferred nitrogen substituents are $R^1$ equal to methyl, and $R^2$ is an alkyl group from 1 to 12 carbon atoms. Most preferred nitrogen substituents are $R^1$ equal to methyl, and $R^2$ is n-propyl or n-butyl.

Preferred substituents at positions 4 and/or 5 of the imidazole ring ($R^3$ and $R^4$) are hydrogen and short alkyl chains of 1 to 6 carbon atoms. More preferred substituents at positions 4 and/or 5 of the imidazole ring are $R^3$ or $R^4$ equal to hydrogen and the remaining position ($R^4$ or $R^3$) equal to a short alkyl chain of 1 to 6 carbon atoms.

A further aspect of the present invention is a one-step synthetic procedure for the production of substituted imidazole-2-thiones by contacting the above defined imidazolium salt starting material with sulfur in the presence of a base. The sulfur for the reaction is preferred in elemental form and may be added as molting sulfur, sublimed sulfur, or precipitated (lac) sulfur. The base for the reaction may be an organic base such as a carbanion salt (for example, alkali metal or alkaline earth metal alkyls or aryls), a trialkylamine, or inorganic bases such as potassium carbonate, trisodium phosphate, calcium hydride, sodium hydride, potassium hydride, calcium oxide, or sodium acetate.

The process of this invention may be conducted preferably between −10 and 200° C., more preferably between 10 and 130° C., and most preferably at temperatures between 80 and 100° C. It is desirable that a liquid phase be present during the entire course of the reaction, but it is a feature of this invention that a solvent need not be added. Many imidazolium salts that are the starting materials for this process are liquid (molting salts) under the preferred reaction conditions. Similarly, many of the product imidazole-2-thiones are also liquids under the preferred reaction conditions. In cases where the starting imidazolium salt or product imidazole-2-thione are not liquid under the preferred reaction conditions, it is a further aspect of this invention that its utility can be extended by the addition of a melting point depressant (antifreeze) that is otherwise inert to the reaction conditions. The melting point depressant (antifreeze) is added to depress the melting points of the starting materials and/or products so that a liquid phase is present in the reaction under the preferred reaction conditions. When using a melting point depressant (antifreeze) in the process, it is desirable to use the minimum amount of said antifreeze necessary to bring the melting point of a component of the reaction mixture into a preferred temperature range for the process. Suitable melting point depressants include (but are not limited to) substituted imidazolium salts that bear no acidic protons (for example any of the various isomers of pentaalkylimidazolium halides), tetraalkylammonium halides, hexaalkylguanidinium halides, and similar low melting salts.

The molar ratio of the starting substituted imidazolium cation to sulfur and to base is ideally 1:1:1. It is also possible in some cases to use proportions that differ from this ideal ratio, but this may result in some waste of the material that is used in excess. When starting material imidazolium salts that possess additional acid functional groups either in the cation or counter anion are employed in the process of this invention, it is desirable to adjust the base stoichiometry to allow for deprotonation of the additional acid sites.

The general process for the invention is to suspend elemental sulfur in the molting imidazolium salt starting material at the preferred operating temperatures for the process, and, with efficient agitation, the base component is then added to the reaction mixture. As the reaction proceeds a by-product salt is formed from the cation of the base and the counter anion of the starting material imidazolium salt. The by-product salt is separated from the product mixture, by filtration, centrifugation, extraction, or another standard technique familiar to one skilled in the art, and the product substituted imidazole-2-thione is isolated and further purified as desired by distillation, recrystallization, extraction, zone refinement, or another standard technique familiar to one skilled in the art. In the event that the starting material imidazolium salt is not liquid at the preferred reaction temperatures, a melting point depressant (antifreeze) as defined above is added to depress the melting point of the starting material imidazolium salt so that it is liquid under the preferred reaction conditions.

The present invention is a solventless one-step process for the production of a variety of substituted imidazole-2-thiones. The solventless aspect of the invention renders the process of this invention more environmentally friendly than conventional industrial or laboratory procedures. The process of this invention offers more flexibility in the choice of base than conventional procedures and compared with industrial or laboratory procedures that use alcohol solvents, the imidazole-2-thiones from this invention are relatively free of malodorous by-products.

Example 1

Preparation of 1-methyl-3-propylimidazole-2-thione (with potassium carbonate as base): A water-jacketed 500 mL flask equipped with ports for addition of solids and blanketed under a dry-nitrogen atmosphere was charged with 200.00 grams (0.98 moles) of 1-methyl-3-propylimidazolium bromide. Lac sulfur, 31.22 grams (0.98 moles), was added as a single portion and the resulting mixture was heated to 80° C. with vigorous stirring. Solid anhydrous potassium carbonate (134.83 grams, 0.98 moles) was added portionwise with adjustment of the cooling rate so that the reaction mixture was held between 80 and 85° C. Carbon dioxide was evolved as the potassium carbonate was added. After the addition of potassium carbonate was completed, the mixture was stirred for an additional 20 hours. The reaction mixture was filtered to remove the inorganic by-products. The filtrate (146 grams, 96%) was a light brown oil that analyzed (by nmr) as pure 1-methyl-3-propylimidazole-2-thione. Distillation of the initially light-brown product from KOH (1 gram) under vacuum (118° C. @ 0.18 mm Hg) gave 1-methyl-3-propylimidazole-2-thione as an odorless off-white oil. $^1$H nmr ($CD_2Cl_2$) δ 6.70

(s, NCH=C, 2H); 3.96 (t, NCH₃, 2H); 3.55 (s, NCH₃, 3H); 1.79 (dq, NCCH₂C, 2H); 0.91 (t, NCCCH₃, 3H).

Example 2

Preparation of 1-methyl-3-propylimidazole-2-thione (with sodium hydride as base): A water-jacketed 1-liter flask equipped with ports for addition of solids and blanketed under a dry-argon atmosphere was charged with 300.00 grams (1.46 moles) of 1-methyl-3-propylimidazolium bromide. Lac sulfur, 46.83 grams (1.46 moles), was added as a single portion and the resulting mixture was heated to 60° C. with vigorous stirring. Sodium hydride 80% dispersion in oil (43.90 grams, 1.46 moles) was added portionwise with adjustment of the cooling rate so that the reaction mixture was held between 60 and 80° C. The reaction is very vigorous and efficient cooling was required. Hydrogen was evolved as the sodium hydride was added. After the addition of sodium hydride was completed, the mixture was stirred for an additional 18 hours. The reaction mixture was filtered to remove the inorganic by-products. The filtrate (226 grams, ~95%) was a brown oil that analyzed (by nmr) as almost pure 1-methyl-3-propylimidazole-2-thione (some mineral oil was evident in the nmr spectrum and could also be seen as a thin layer over the desired product). Distillation of the crude product from KOH (1 gram) under vacuum (200° C. @ 0.20 mm Hg) gave 1-methyl-3-propylimidazole-2-thione (210 grams 92%) as an odorless light yellow oil.

Example 3

Preparation of 1-methyl-3-propylimidazole-2-thione (with calcium oxide as base): A water-jacketed 1-liter flask equipped with ports for addition of solids and blanketed under a dry-nitrogen atmosphere was charged with 300.00 grams (1.46 moles) of 1-methyl-3-propylimidazolium bromide. Lac sulfur, 46.83 grams (1.46 moles), was added as a single portion and the resulting mixture was heated to 80° C. with vigorous stirring. Calcium oxide (40.93 grams, 0.73 moles) was added slowly at 80° C. After the addition of calcium oxide was completed, the mixture was heated to 105° C. and stirred for an additional 26 hours. Cooling of the reaction mixture below approximately 80° C. resulted in crystallization of large quantities of $CaBr_2$, this should be avoided. At 90° C. 170 mL water was added to extract the calcium bromide by-product. The mixture was quickly cooled to 23° C. and the water/calcium bromide layer was separated from the organics. The organic layer was dried over anhydrous sodium sulfate to give the crude imidazole-2-thione (193 grams, 85%). Distillation of the crude product from KOH (1 gram) under vacuum (200° C. @ 0.20 mm Hg) gave 1-methyl-3-propylimidazole-2-thione (189 grams 83%) as an odorless light yellow oil.

Example 4

Preparation of 1-methyl-3-propylimidazole-2-thione (with trisodium phosphate as base): A water-jacketed 1-L flask equipped with ports for addition of solids and blanketed under a dry-nitrogen atmosphere was charged with 200 grams (0.98 moles) of 1-methyl-3-propylimidazolium bromide. Lac sulfur, 31 grams (0.98 moles), was added as a single portion and the resulting mixture was heated to 80° C. with vigorous stirring. After a consistent uniformity was reached in the suspension, solid anhydrous trisodium phosphate (160 grams, 0.98 moles) was added portionwise so that the temperature could be maintained at about 80° C. The mixture was stirred for an additional 40 hours after the addition was complete. The reaction mixture was filtered to remove the inorganic by-products. The filtrate (152 grams, 99%) was a brown oil that analyzed (by nmr) as pure 1-methyl-3-propylimidazole-2-thione. Distillation of the initial brown product from KOH (1 gram) under vacuum (200° C. @ 0.20 mm Hg) gave 1-methyl-3-propylimidazole-2-thione as an odorless light-yellow oil.

Example 5

Preparation of 1-methyl-3-n-octylimidazole-2-thione (with methyl-DABCO as base, plus added antifreeze): A water-jacketed 1-liter flask equipped with ports for addition of solids and blanketed under a dry-argon atmosphere was charged with 1-methyl-3-n-octylimidazolium bromide (200.0 grams, 0.73 mol), 23.4 grams (0.73 mol) lac sulfur and 1 gram 1-butyl-2,3,4,5-tetramethyl-imidazolium tetrafluoroborate (as melting point depressant) and heated to 80° C. MethylTEDA (2-methyl-1,4-diazabicyclo[2.2.2]octane) 92.0 grams (0.73 mol) was added as a single portion to the reaction mixture with vigorous stirring. After 3 hours nmr analysis of the reaction mixture showed the reaction to be proceeding slowly. The temperature was increased to 100° C. and the heating was continued for an additional 33 hours. The reaction mixture was checked by $^1$H nmr to assure completion. The brown mixture was cooled to 50° C. and filtered through a course fritted glass funnel to remove some solids. The filtrate was washed three times with 100 ml water and then vacuum distilled in a short path molecular still from KOH to give 122 grams (74%) of a yellow oil. The $^1$H nmr (acetone-$d_6$): δ 7.02 (m, NCH=C, 2H); 4.02 (t, NCH₂, 2H), 3.54 (s, NCH₃, 3H); 1.75 (m, NCCH₂, 2H); 1.30 (m, NCC(CH₂)₅, 10H); 0.86 (m, (C)₇CH₃, 3H).

Example 6

Preparation of 1-butyl-3-methylimidazole-2-thione (with sodium hydride as base): A water-jacketed 1-liter flask equipped with ports for addition of solids and blanketed under a dry-nitrogen atmosphere was charged with 1-butyl-3-methylimidazolium chloride (400.0 grams, 2.3 mol) and 73.6 grams (2.3 mol) lac sulfur and heated to 70° C. Sodium hydride (60% in mineral oil) 92.0 grams (2.3 mol) was added portionwise to the reaction mixture with vigorous stirring and cooling to retain the reaction temperature below 90° C. The reaction was very exothermic and hydrogen evolution was vigorous. The mixture was stirred for an additional 1 hour after the hydrogen evolution was complete and was then cooled to 45° C. and filtered to remove the precipitated solids. The brown oily filtrate was vacuum distilled, 107° C./0.01 mm Hg from 2 grams KOH pellets to give 1-butyl-3-methyl-imidazole-2-thione as a clear to slightly yellow colored oil (355.5 grams, 91%). The $^1$H nmr (acetonitrile-$d_3$) δ 6.84 (s, NCH=C, 2H); 3.96 (t, NCH₂, 2H); 3.49 (s, NCH₃, 3H); 1.63 (tt, NCCH₂, 2H); 1.30 (tq, NCCCH₂C, 2H); 0.93 (t, CCCCH₃, 3H).

What is claimed is:
1. A process of making substituted imidazole-2-thiones of the formula:

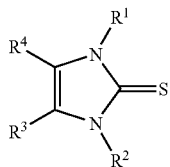

wherein:
R$^1$ and R$^2$ are independently hydrocarbyl or substituted hydrocarbyl;
R$^3$ and R$^4$ are independently hydrogen, hydrocarbyl, substituted hydrocarbyl, ether, or thioether;
consisting of the following step:
in the absence of a solvent, contacting a base, sulfur, and

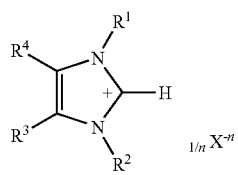

imidazolium salt of the formula:
wherein:
R$^1$ and R$^2$ are independently hydrocarbyl or substituted hydrocarbyl;
R$^3$ and R$^4$ are independently hydrogen, hydrocarbyl, substituted hydrocarbyl, ether, or thioether;
X$^{-n}$ is an anion that is the counterion to the imidazolium cation and n is the number of anionic charges on X.

2. The process of claim 1, conducted at a temperature of from about −10 to about 200° C.

3. The process of claim 2, conducted at a temperature of from about 10 to about 130° C.

4. The process of claim 3, conducted at a temperature of from about 80 to about 100° C.

5. The process of claim 1, wherein the base is an alkali metal hydride.

6. The process of claim 1, wherein the base is trisodium phosphate.

7. The process of claim 1, wherein the base is potassium carbonate.

8. The process of claim 1, wherein the base is calcium oxide.

9. The process of claim 1, wherein R$^1$ and R$^2$ are alkyl substituents.

10. The process of claim 1, wherein R$^3$ and R$^4$ are alkyl substituents.

11. The process of claim 9, wherein R$^3$ and R$^4$ are independently hydrogen or alkyl substituents.

12. The process of claim 9, wherein R$^3$ and R$^4$ are hydrogen.

13. The process of claim 12, wherein R$^1$ and R$^2$ are methyl and n-propyl respectively.

14. The process of claim 1, wherein a melting point depressant is added to bring the process operating temperature in to a preferred temperature range.

15. The process of claim 14, wherein R$^1$ and R$^2$ are isopropyl; R$^3$ and R$^4$ are hydrogen; and the melting point depressant is a pentaalkylimidazolium salt.

16. The process of claim 15, wherein the melting point depressant is 1-butyl-2,3,4,5-tetramethylimidazolium tetrafluoroborate.

17. The process of claim 1 wherein the process is conduced under an inert gas.

18. The process of claim 17 wherein the inert gas is selected from nitrogen or argon, or a mixture thereof.

19. The process of claim 14 wherein the process is conducted under an inert gas.

20. The process of claim 19 wherein the inert gas is nitrogen or argon, or a mixture thereof.

* * * * *